United States Patent
Margulis

(10) Patent No.: US 9,907,701 B2
(45) Date of Patent: Mar. 6, 2018

(54) TYMPANIC MEMBRANE REPAIR DEVICE

(75) Inventor: Ariel Margulis, Tel-Aviv (IL)

(73) Assignee: MOR RESEARCH APPLICATIONS LTD., Tel-Aviv (IL)

( * ) Notice: Subject to any disclaimer, the term of this patent is extended or adjusted under 35 U.S.C. 154(b) by 232 days.

(21) Appl. No.: 14/003,802

(22) PCT Filed: Mar. 8, 2012

(86) PCT No.: PCT/IL2012/050076
§ 371 (c)(1),
(2), (4) Date: Sep. 8, 2013

(87) PCT Pub. No.: WO2012/120513
PCT Pub. Date: Sep. 13, 2012

(65) Prior Publication Data
US 2013/0345722 A1  Dec. 26, 2013

Related U.S. Application Data

(60) Provisional application No. 61/450,175, filed on Mar. 8, 2011.

(51) Int. Cl.
| | |
|---|---|
| *A61B 17/08* | (2006.01) |
| *A61D 1/00* | (2006.01) |
| *A61F 11/00* | (2006.01) |
| *A61F 2/18* | (2006.01) |

(52) U.S. Cl.
CPC ............. *A61F 11/004* (2013.01); *A61F 2/18* (2013.01); *A61F 2002/183* (2013.01)

(58) Field of Classification Search
CPC .... A61F 2002/183; A61F 2/18; A61F 11/004; A61F 11/00; A61F 11/002; A61F 2002/4435; A61M 2210/0668
USPC .................... 623/10; 606/109, 142, 213, 215
See application file for complete search history.

(56) References Cited

U.S. PATENT DOCUMENTS

| | | | |
|---|---|---|---|
| 4,641,651 A | | 2/1987 | Card |
| 5,236,455 A | * | 8/1993 | Wilk .......................... A61F 2/18 128/890 |
| 5,254,133 A | | 10/1993 | Seid |
| 5,501,700 A | | 3/1996 | Hirata |
| 5,643,300 A | | 7/1997 | Hirata |
| 6,309,419 B1 | | 10/2001 | De Juan, Jr. et al. |
| 2002/0151974 A1 | | 10/2002 | Bonassar et al. |
| 2004/0181185 A1 | | 9/2004 | Lee |

(Continued)

FOREIGN PATENT DOCUMENTS

| | | |
|---|---|---|
| CN | 2162943 | 4/1994 |
| GB | 108797 | 8/1917 |

(Continued)

OTHER PUBLICATIONS

"EpiDisc Tympanic Membrane Perforation Patch Kit", Medtronic, Nov. 14, 2014.

(Continued)

*Primary Examiner* — Katherine M Shi
(74) *Attorney, Agent, or Firm* — Roach Brown McCarthy & Gruber P.C.; Kevin D. McCarthy

(57) ABSTRACT

A method for repairing a perforation in a tympanic membrane comprising attaching a single patch to an undersurface of the tympanic membrane covering the perforation.

12 Claims, 16 Drawing Sheets

(56) References Cited

U.S. PATENT DOCUMENTS

| 2008/0262468 | A1* | 10/2008 | Clifford | ............... | A61F 11/002 |
| | | | | | 604/501 |
| 2009/0297533 | A1* | 12/2009 | Lichter | ............... | A61K 9/0046 |
| | | | | | 424/142.1 |
| 2009/0299379 | A1* | 12/2009 | Katz | ..................... | A61F 11/002 |
| | | | | | 606/109 |

FOREIGN PATENT DOCUMENTS

| JP | 2006240441 | 9/2006 |
| KR | 20080040516 | 5/2008 |
| WO | WO 2012/120513 | 9/2012 |

OTHER PUBLICATIONS

"EpiFilm and EpiDisc Otologic Laminae", Ear Packing Products Medtronic, Nov. 14, 2014.

"Procedures and Techniques for Tympanoplasty and Ossicular Reconstruction", Medtronic, Nov. 14, 2014.

Communication Under Rule 71(3) EPC dated Jul. 16, 2014 From the European Patent Office Re. Application No. 12715440.9.

International Search Report and the Written Opinion dated Jun. 6, 2012 From the International Searching Authority Re. Application No. PCT/IL2012/050076.

International Preliminary Report on Patentability dated Sep. 19, 2013 From the International Bureau of WIPO Re. Application No. PCT/IL2012/050076.

\* cited by examiner

TYMPANIC MEMBRANE REPAIR DEVICE

RELATED APPLICATIONS

This application is a National Phase of PCT Patent Application No. PCT/IL2012/050076 having International filing date of Mar. 8, 2012, which claims the benefit of priority under 35 USC § 119(e) of U.S. Provisional Patent Application No. 61/450,175 filed on Mar. 8, 2011. The contents of the above applications are all incorporated by reference as if fully set forth herein in their entirety.

FIELD AND BACKGROUND OF THE INVENTION

The present invention, in some embodiments thereof, relates to the field of Tympanoplasty and, more particularly, but not exclusively, to a device and a method for repairing a perforation in a Tympanic membrane.

Tympanoplasty is a surgical treatment for repairing a perforation in the tympanic membrane (commonly known as "eardrum") and defects in one or more of the ossicular bones. Perforations in the eardrum may be the result of a birth defect, or may be attributed to ear/nose/throat infections, physical ear injury, exposure to high noise levels, aging, among other contributing factors.

Methods for repairing eardrum perforations and devices used in tympanoplastic surgery are known in the art.

U.S. Pat. Nos. 5,501,700 and 5,643,300 to Hirata relates to "an eardrum perforation patch and an eardrum undersurface scraper for application of the patch. The eardrum perforation patch comprises double plates connected together with a coupler and these elements are made of artificial material. The plates comprise a supporting piece and a closure piece. After being inserted into the tympanic perforation the closure piece pinches the perforation margin and it stays steadily in place until it changes to a new part of the tympanic membrane. The eardrum undersurface scraper comprises a shaft, a neck and a head with a blade edge. The neck is curved at an angle of more than 90 degrees, twisted and rotated, so that the blade edge gains access to target points behind the tympanic membrane and scrapes and entirely rakes out the mucosal barrier on the undersurface grafting bed of the tympanic membrane through the tympanic perforation. The combination of the eardrum perforation patch and the eardrum undersurface scraper is useful in repairing the tympanic perforation".

U.S. Pat. No. 5,236,455 to Wilk et al. relate to "a device for repairing a tympanic membrane comprises a patch provided on one side with an adhesive layer, and an elongate tubular applicator member having a proximal end and a distal end. The patch is removably attached via suction to the distal end of the tubular applicator member so that the adhesive layer faces away from the elongate applicator member. The proximal end of the tubular applicator member is temporarily closed or sealed to maintain the suction force, thereby holding the tympanic patch to the distal end of the applicator tube while the tube is being inserted through the auditory canal. Upon a pressing of the patch against the ear drum so that the patch covers the perforation, the proximal end of the tube is released to pressurize the tube channel with ambient air. This pressurization releases the patch and allows it to adhere to the tympanic membrane".

U.S. Pat. No. 4,641,651 to Card discloses "an ossicular replacement prosthesis is configured to have its tympanic membrane-facing end self-attached to a cartilage plug forced there against. Self-attachment is achieved either by a prosthesis projection penetrating the plug, a prosthesis portion enclosing at least part of the plug, or adhesive attachment between the plug and prosthesis. A cartilage punch is provided which removes a cartilage plug of uniform thickness from a patient's tragus, retains the plug after removal and then forcefully urges the plug against the prosthesis to effect self-attachment. The punch includes a reciprocatable annular cutting member and a stage surface. Tragal cartilage is inserted between the cutting member and the stage, and the cartilage plug is cut and retained in the cutting member by forcing the cutting member toward the stage to pierce the tragel cartilage. The prosthesis is then placed on the stage so that the retained cartilage plug can be forced thereagainst by again translating the cutting member toward the stage".

U.S. Pat. No. 6,309,419 to de Juan, Jr. et al. discloses "a tympanic membrane prosthesis is provided that includes, in combination, a generally flat, planar membrane sized to overlay a tear or perforation in the tympanic membrane and having at least one preformed perforation, and at least one mechanical fixation device for fixing the membrane to the tympanic membrane of a patient. Each mechanical fixation device is a tack component including a sharp, piercing distal end, an enlarged proximal end and a shaft extending therebetween. A tack insertion device is provided to guide the tack to and through the tear covering membrane".

Additional background art includes U.S. Patent Application Publication No. 2002/0151974, U.S. Pat. No. 5,254,133, China Patent No. CN2162943, and Korea Patent No.KR20080040516.

SUMMARY OF THE INVENTION

According to one aspect of the present invention, there is provided a method for repairing a perforation in a tympanic membrane comprising attaching a single patch to an undersurface of the tympanic membrane covering the perforation.

In some exemplary embodiments, the method includes inserting the patch through the perforation.

In some exemplary embodiments, the method includes pulling the patch in a proximal direction against the undersurface.

In some exemplary embodiments, the method includes attaching the patch with a biocompatible adhesive.

In some exemplary embodiments, the method includes debriding peripheral tissue surrounding the perforation.

In some exemplary embodiments, the method includes rotating a cutting edge against the peripheral tissue.

In some exemplary embodiments, the method includes punching a cutting edge through the peripheral tissue.

In some exemplary embodiments, the method includes extracting the peripheral tissue.

In some exemplary embodiments, the method includes monitoring the repair of the perforation with a micro-otoscope.

According to one aspect of the present invention, there is provided a device for attaching a patch to an undersurface of a tympanic membrane, comprising a patch guiding mechanism including a rod for inserting the patch through a perforation in the tympanic membrane, and a debridement mechanism including a cutting edge for cutting tissue surrounding the perforation.

In some exemplary embodiments, the rod includes a distal end adapted to accommodate mechanical coupling of the patch.

In some exemplary embodiments, the distal end includes a spring-loaded clamp for grasping the patch.

In some exemplary embodiments, the cutting edge is a circular cutting edge.

In some exemplary embodiments, the cutting edge is rotatable.

In some exemplary embodiments, the device includes a patch release mechanism for reversely releasing the patch following attachment to the undersurface.

In some exemplary embodiments, the patch release mechanism includes a hollow tube slidably fitting over the distal end.

In some exemplary embodiments, the hollow tube is adapted to exert a radial force on the distal end of the rod.

In some exemplary embodiments, the patch release mechanism includes a release lever for proximally pulling the hollow tube.

In some exemplary embodiments, the device includes a device alignment mechanism for substantially axially aligning the device when inserted in the auditory canal.

In some exemplary embodiments, the device alignment mechanism includes an alignment receptacle for aligning the patch guiding mechanism with the perforation.

In some exemplary embodiments, the device alignment mechanism includes a speculum.

In some exemplary embodiments, the device includes an adhesive application mechanism for administering an adhesive through the device to the patch.

In some exemplary embodiments, the adhesive application mechanism includes an adhesive insertion adapter through which the adhesive is poured into the device.

In some exemplary embodiments, the adhesive insertion adapter is attached to a hollow rod in the patch guiding mechanism having a conduit fluidly connecting the adhesive insertion adapter with the patch.

In some exemplary embodiments, the patch includes a surface texture conducive to epithelial cell growth.

In some exemplary embodiments, the patch includes hyaluronic acid.

In some exemplary embodiments, a diameter of the patch is in a range from 2 mm-10 mm.

In some exemplary embodiments, the patch includes a flexible material.

In some exemplary embodiments, the patch includes a biodegradable material.

In some exemplary embodiments, the device is configured for disposing following a single use.

According to one aspect of the present invention, there is provided a kit for repairing a perforation in a tympanic membrane comprising a device for attaching a patch to an undersurface of the tympanic membrane, and a patch.

In some exemplary embodiments, the kit includes an adhesive for attaching the patch to the undersurface.

In some exemplary embodiments, the kit includes an adhesive applicator for applying the adhesive to the device.

In some exemplary embodiments, the kit includes a micro-otoscope.

In some exemplary embodiments, the kit includes a single-use, disposable device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings.

DESCRIPTION OF SPECIFIC EMBODIMENTS OF THE INVENTION

Figure 1:
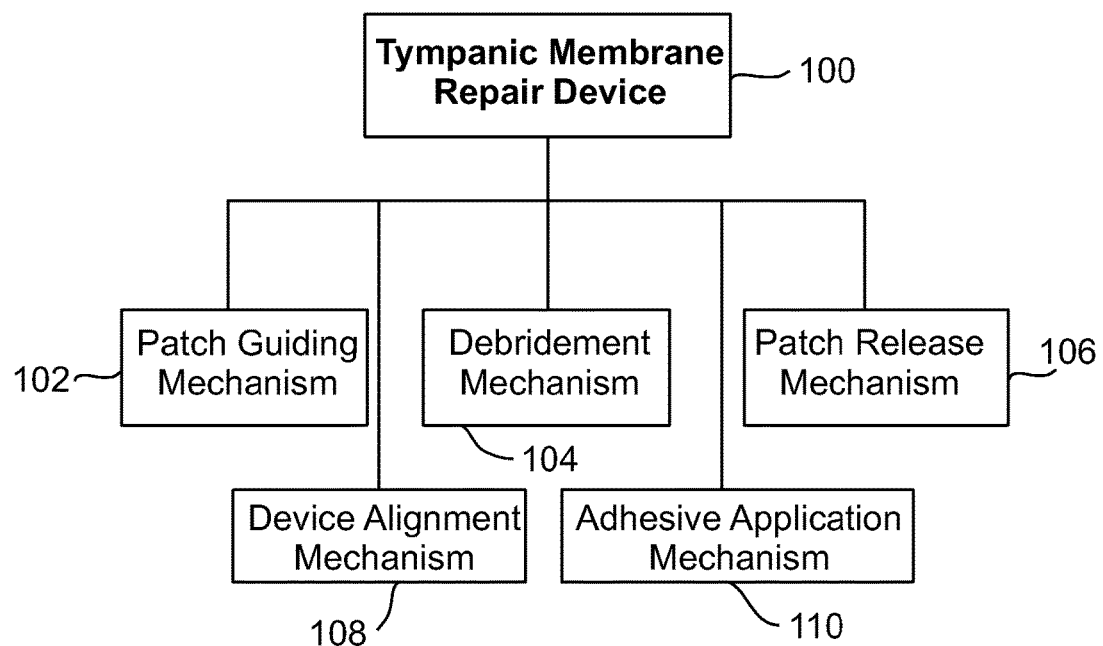
FIG. 1 schematically illustrates an exemplary tympanic membrane repair device, according to an embodiment of the present invention.

The present invention, in some embodiments thereof, relates to the field of Tympanoplasty and, more particularly, but not exclusively, to a device and a method for repairing a perforation in a Tympanic membrane.

An aspect of some embodiments of the present invention relates to a method for relatively rapidly repairing a perforation in a tympanic membrane including debriding peripheral membrane tissue surrounding the perforation and adhering a flexible patch to the membrane's undersurface covering the perforation. An undersurface of the tympanic membrane is the surface of the membrane bounding on the middle ear. The method can allow, in some exemplary embodiments, for repairing the perforation in an estimated period of time ranging from 5 to 20 minutes, from the time the device is introduced by the physician into an auditory canal of a patient. The method can further allow, in some exemplary embodiments, for repairing all types of tympanic membrane perforations excluding large marginal perforations (where the perforation includes a border/margin of the tympanic membrane).

In some exemplary embodiments, the patch is guided down the auditory canal of the patient and inserted through the perforation. Optionally, debridement increases a distance from a center of the perforation to a border of the perforation by at least, 1 mm. Debridement removes the injured or infected tissue surrounding the perforation, resulting in faster epithelial tissue growth across the patch and natural tissue sealing of the perforation. Optionally, debridement of the peripheral tissue is performed following inserting the patch through the perforation. Alternatively, debridement is performed prior to inserting the patch through the perforation.

In some exemplary embodiments, the method includes using a same device for introducing the patch through the perforation, attaching the patch to the undersurface, and performing the debridement. Optionally, the device is inserted into the auditory canal only once during the whole procedure. Alternatively, a separate cutting device is used for performing debridement. Optionally, the cutting device is introduced together with the single device. Optionally, the method does not require administering a painkiller and/or other medication to the patient. Alternatively, the painkiller and/or other medication are locally administered. Optionally, the device is also used for applying the painkiller and/or medication.

In some exemplary embodiments, the method includes using a micro-otoscope or other suitable instrument known in the art for monitoring the procedure. Optionally, the micro-otoscope is mechanically coupled to the device. Alternatively, the micro-otoscope is separate from the device. Alternatively, the method includes using a guidewire for guiding the device with the patch through the auditory canal and through the perforation into the middle ear, obviating a use of monitoring equipment.

In some exemplary embodiments, the patch is of a biocompatible material and is attached to the undersurface of the membrane with a biocompatible adhesive. Optionally, the adhesive is applied to the patch following inserting the patch through the perforation. Optionally, the adhesive is "instant" adhering type glue such as, for example, Dermabond by Ethicon™. Optionally, an amount of glue applied to the patch is between, 20-150 microliters. Alternatively, the adhesive is applied prior to inserting the patch through the perforation. Alternatively, the adhesive is applied prior to guiding the patch down the auditory canal. Alternatively, the adhesive is applied during production of the patch. Alternatively, the patch is self-adhering.

In some exemplary embodiments, the patch includes a surface texture for promoting epithelial tissue growth for closing the perforation. Optionally, the patch is biodegradable. Optionally, the patch includes Alloderm® and/or hyaluronic acid. Alternatively, the patch is not biodegradable and remains implanted in the patient's ear. The patch may be of a diameter in a range from 2 mm-10 mm, for example 3 mm, 4 mm, 5 mm, 6 mm, 8 mm, 9 mm. Optionally, the diameter of the patch is greater than a size of the perforation by 1 mm or more, for example, 2 mm, 3 mm, 4 mm, 6 mm, or greater. Alternatively, the patch includes a non-circular shape. Optionally, the non-circular patch includes an area similar to that of the previously mentioned circular patch. Optionally, the patch covers an area of the undersurface not less than 110% of the size of the perforation, for example, 112%, 115%, 125%, 150%, 200%, or more. Optionally, the patch overlays the borders of the perforation by at least, 1 mm, 1.2 mm, 1.5 mm, 2 mm, or greater. Alternatively, the patch is single-sized and is cut by the physician according to a size of the perforation. Optionally, the single-sized patch is of a large size for allowing several patches to be cut from the single-sized patch. Optionally, the single-sized patch may have a diameter ranging from 3 mm-20 mm, for example, 4 mm, 6 mm, 8 mm, 10 mm, 12 mm, 15 mm, 18 mm, 19 mm. Alternatively, the single-sized patch includes an area the same as that of the circular single-sized patch.

An aspect of some embodiments of the present invention relates to a tympanic membrane repair device insertable through an auditory canal of a patient for adhering a flexible patch to the membrane's undersurface covering a perforation, and for performing debridement of peripheral membrane tissue surrounding the perforation. Optionally, the device is adapted to flatly attach the patch to the undersurface. Optionally, the diameter of the perforation is increased by the debridement. Optionally, the device is used for guiding the flexible patch through the perforation into the middle ear. A single device for performing these actions is potentially advantageous over techniques known in the art as only one device is inserted a single time into the patient's auditory canal. This allows for the repair to be performed quickly, substantially saving on physician time and possible associated medical costs, and potentially reduces patient discomfort.

In some exemplary embodiments, the device includes a patch guiding mechanism which secures the patch to the device while being guided down the auditory canal and through the perforation. Optionally, the patch guiding mechanism secures the patch while being adhered to the undersurface of the tympanic membrane. Optionally, the patch is supported by a gel while being adhered to the undersurface. In some exemplary embodiments, the patch guiding mechanism includes a spring-loaded arrangement for clasping the patch. Alternatively, the patch guiding mechanism includes a male/female type fastening mechanism for securing the patch. Alternatively, the patch guiding mechanism includes a hook-and-fastener type of fastening mechanism. Alternatively, the patch guiding mechanism is connected to a vacuum device adapted to apply a sucking force to the patch for securing the patch. Optionally, the patch is secured to the device prior to insertion into the auditory canal. Alternatively, the patch is pre-attached to the patch guiding mechanism at the device manufacturer. Optionally, the patch guiding mechanism comes as a kit with the patch, the patch guiding mechanism being replaceable following one-time use.

In some exemplary embodiments, the device includes a patch release mechanism for releasing the patch once attached to the undersurface of the tympanic membrane. Optionally, the patch is released by the physician activating a patch release lever included in the patch release mechanism. Optionally, the patch is released by releasing the clamping action of the spring-loading clamping mechanism. Alternatively, the patch is released by a pulling action exerted on the patch while being attached, or already attached, to the undersurface.

In some exemplary embodiments, the device includes a debridement mechanism for cutting away tympanic membrane tissue surrounding the perforation prior to adhering the patch. Optionally, the debridement mechanism includes a circular cutting edge (blade) for performing the cutting. Optionally, cutting is performed rotating the circular cutting edge so that the surrounding membrane is progressively cut along a circumference of the enlarged perforation. Alternatively, cutting is performed by punching] through the tissue, cutting the surrounding membrane at once. Optionally, the circular cutting edge is of a diameter ranging from 2 mm-19 mm, for example, 3 mm, 5 mm, 8 mm, 12 mm, 15 mm, 18 mm. Optionally, an anvil-like arrangement is included for supporting the membrane while being punched through by the blade. Optionally, the cut tissue is fitted within the periphery of the circular cutting edge and is removed from the auditory canal together with the device. Alternatively, the cutting edge is non-circular. Additionally, the device includes a cover for maintaining the cutting edge unexposed until the debridement is to be performed. Alternatively, the blade is introduced through the device and is remotely operated by the physician for cutting the tissue. Alternatively, the blade includes a scissor-like arrangement for effecting the cutting of the surrounding membrane. Alternatively, heating may be used for cutting the surrounding membrane. Alternatively, the debridement mechanism includes an arrangement for extracting the cut tissue from the auditory canal, such as, for example, a grasping mechanism. Alternatively, the cut tissue is not removed, and is left inside the middle ear.

In some exemplary embodiments, the device includes a device alignment mechanism for allowing the physician to properly align the device inside the patient's ear and for anchoring the device while operated by the physician. Optionally, the alignment mechanism includes a speculum fitted over the device and insertable into the ear. Optionally, the speculum provides radial alignment of the device within the auditory canal. Optionally, the speculum are axially positioned within the auditory canal. Alternatively, the device does not include an alignment mechanism and is aligned by the physician while holding the device. Optionally, the physician uses a second hand to align the device.

In some exemplary embodiments, the device includes an adhesive application mechanism for introducing the adhesive into the device from outside the ear and for conducting the adhesive to the patch. Optionally, the device includes an adhesive insertion adaptor for attaching a container with the adhesive for administering the adhesive to the patch. Optionally, the container includes a premeasured amount of the adhesive required for applying to the patch. Alternatively, the device includes a container which is filled with the premeasured amount of adhesive. Optionally, the container in the device is replaceable. In some exemplary embodiments, the device includes a conduit for adhesive flow to the patch. Alternatively, the patch is self-adhering and the adhesive insertion adapter, the container, the conduit, or the adhesive are not required.

In some exemplary embodiments, the device may be used for treating a condition where a retraction pocket has been created in the tympanic membrane. Optionally, the debridement mechanism is used to cut the retraction pocket and surrounding tissue leaving an opening through which the patch is inserted and attached to the undersurface.

An aspect of some embodiments of the present invention relates to a tympanic membrane repair device which is made for a one-time (single) use. Optionally, the device is disposable following the one-time use. Optionally, the device is manufactured using relative inexpensive components and materials, for example, using plastic components and mass-production plastic molding techniques. Optionally, the device is pre-sterilized during manufacture so that in-situ sterilization is not required. Optionally, the device does not require cleaning or removal of traces of adhesive possibly remaining in the device from the application of the adhesive to the patch.

An aspect of some embodiments of the present invention relates to a tympanic membrane repair kit including a single use tympanic membrane repair device. Alternatively, the repair kit includes a multiple use device. Optionally, the repair kit includes one or more patches. Optionally, the repair kit includes the adhesive. Optionally, the repair kit includes an adhesive applicator. Alternatively, the patches are self-adhering and the adhesive and the adhesive applicator are not required. Optionally, the repair kit includes an otoscope separately insertable into the auditory canal from the tympanic membrane repair device. Additionally or alternatively, the separate otoscope is attachable to the device for insertion into the auditory canal together with the device.

Before explaining at least one embodiment of the invention in detail, it is to be understood that the invention is not necessarily limited in its application to the details of construction and the arrangement of the components and/or methods set forth in the following description and/or illustrated in the drawings.

Referring now to the drawings, FIG. 1 schematically illustrates an exemplary tympanic membrane repair device 100, according to an embodiment of the present invention. Optionally, tympanic membrane repair device 100 is used by a physician for guiding a flexible patch down an auditory canal and through a perforation in the tympanic membrane into the middle ear of a patient. Optionally, device 100 is used by the physician for attaching the patch to an undersurface of the tympanic membrane. Additionally or alternatively, device 100 is used by the physician for performing debridement of tissue peripherally surrounding the perforation.

In some exemplary embodiments of the invention, tympanic membrane repair device 100 includes a patch guiding mechanism 102 which secures the patch as it is guided down the auditory canal and through the perforation in the tympanic membrane. Optionally, patch guiding mechanism 102 secures the patch while being adhered to the undersurface.

In some exemplary embodiments, tympanic membrane repair device 100 includes a debridement mechanism 104 for cutting away membrane tissue peripherally surrounding the perforation. Alternatively, debridement mechanism 104 is a separate cutting device which is introduced together with device 100 for accessing the debridement area. Alternatively, debridement mechanism 104 is a separate cutting device which is introduced separately from device 100 for accessing the debridement area. Optionally, debridement mechanism 104 is introduced through device 100.

In some exemplary embodiments, tympanic membrane repair device 100 includes a patch release mechanism 106 for releasing the patch from patch guiding mechanism 102 following attachment to the undersurface of the tympanic membrane.

In some exemplary embodiments, tympanic membrane repair device 100 includes a device alignment mechanism 108 for assisting the physician to properly align and anchor device 100 when inserted in the auditory canal. Optionally, device alignment mechanism 108 includes alignment/anchoring components known in the art and suitable to be fitted onto device 100.

In some exemplary embodiments, tympanic repair device 100 includes an adhesive application mechanism 110 which serves for applying the adhesive to the patch prior to adhering to the undersurface. Optionally, adhesive application mechanism 110 includes a receptacle for receiving an adhesive applied exteriorly to the ear and a conduit for conducting the adhesive through device 100 to the patch. Alternatively, adhesive application mechanism 110 includes a pre-filled container with adhesive and a conduit leading to the patch. Optionally, the patch is self-adhering and adhesive application mechanism 110 is not included in device 100.

Figure 2:
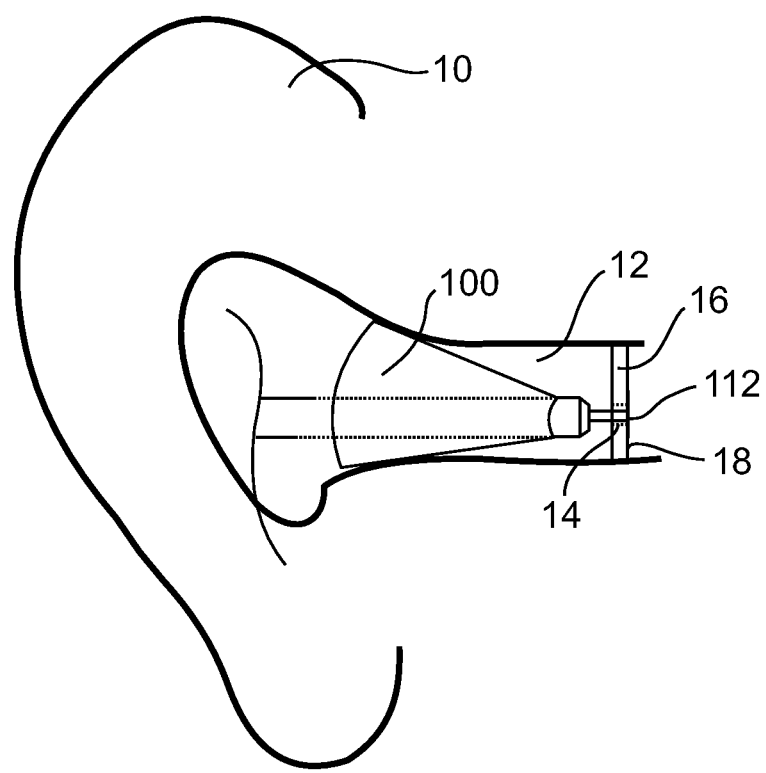
FIG. 2 schematically illustrates the tympanic membrane repair device of FIG. 1 positioned in an ear, inside the auditory canal, according to some exemplary embodiments of the present invention.

Reference is also made to FIG. 2 which schematically illustrates tympanic membrane repair device 100 positioned in an ear 10, inside the auditory canal 12, according to some exemplary embodiments of the present invention. Device 100 is used to repair a perforation 14 in a tympanic membrane 16. Repair is done by using device 100 to introduce a patch 112 through perforation 14 for adhering the patch to an undersurface 18 of tympanic membrane 16. In some exemplary embodiments, device 100 is used to perform debridement on perforation 14 prior to adhering patch 112 to undersurface 18. In some exemplary embodiments, the adhesive is introduced from outside ear 10 and flows through device 100 onto patch 112. Alternatively, patch 112 is self-adhering.

Figure 3:
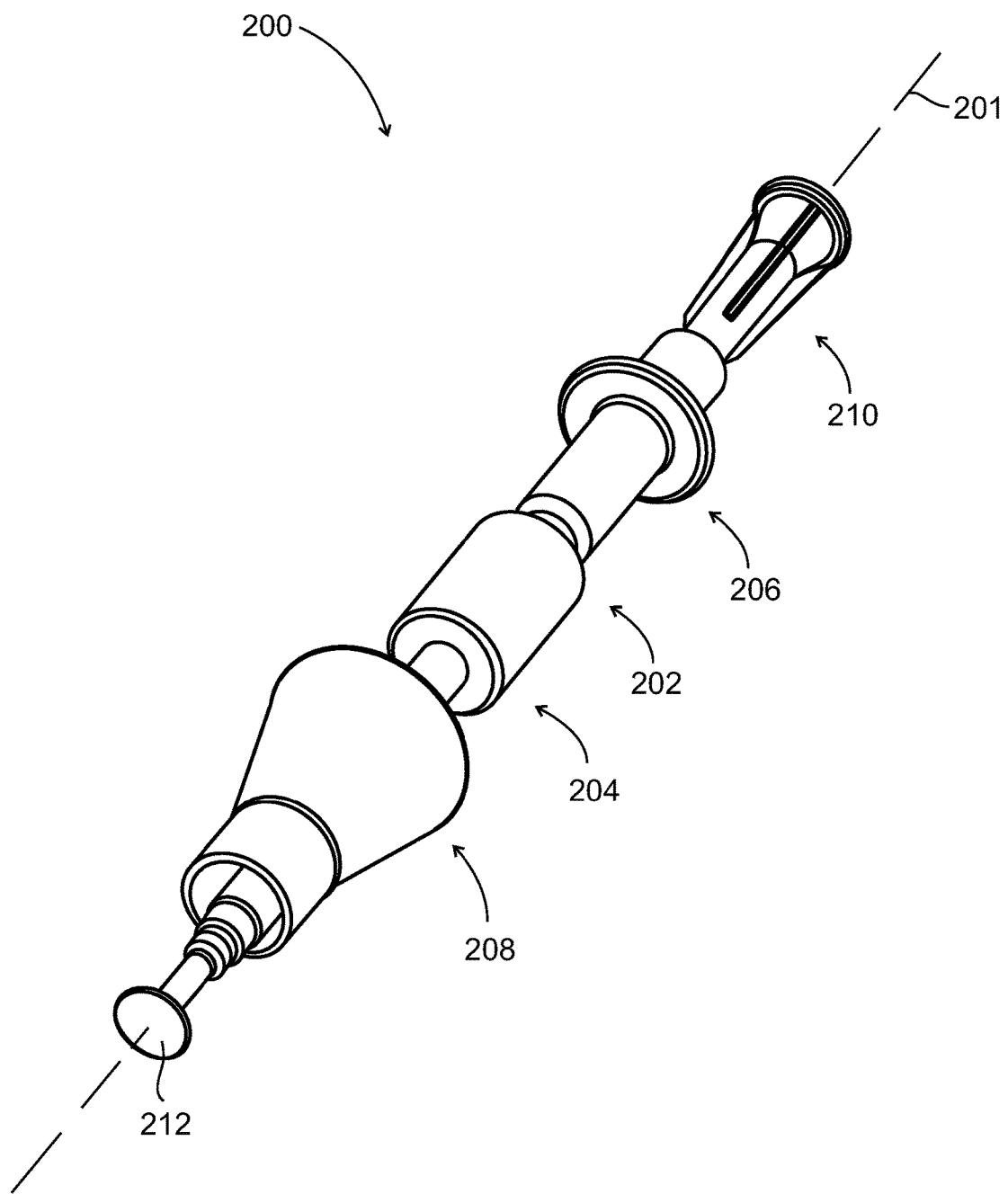
FIG. 3 schematically illustrates an exemplary tympanic membrane repair device for applying a patch to a perforation on a tympanic membrane, according to some embodiments of the present invention.

Reference is now made to FIG. 3 which schematically illustrates an exemplary tympanic membrane repair device 200 for applying a patch 212 to a perforation on a tympanic membrane, according to some embodiments of the present invention. In some exemplary embodiments, tympanic membrane repair device 200 includes a patch guiding mechanism 202, a debridement mechanism 204, a patch release mechanism 206, a device alignment mechanism 208, and an adhesive application mechanism 210. In some exemplary embodiments, device 200 including device mechanisms 202-210, are similar to device 100 including device mechanisms 102-110.

In some exemplary embodiments, device 200 includes an elongated, substantially cylindrical shape for facilitating partial insertion of the device into the patient's auditory canal while a portion of the device remains external to the auditory canal. Optionally, the portion of device 200 external to the auditory canal includes components of the various device mechanisms 202, 204, 206, and 210 which are acted upon by the physician for operating the device. Optionally, the physician operates device 200 using only one hand.

In some exemplary embodiments, device 200 is configured with device mechanisms 202-210 distributed along a longitudinal axis 201 of the device allowing the mechanisms to be independently operated by the physician. Optionally, device 200 includes a telescopic configuration with the device mechanisms 202, 206 and 204 concentrically overlaid one on the other (in the same order), allowing the physician to independently displace debridement mechanism 204 and patch release mechanism 206 along longitudinal axis 201 relative to patch guiding mechanism 202.

Figure 4A:
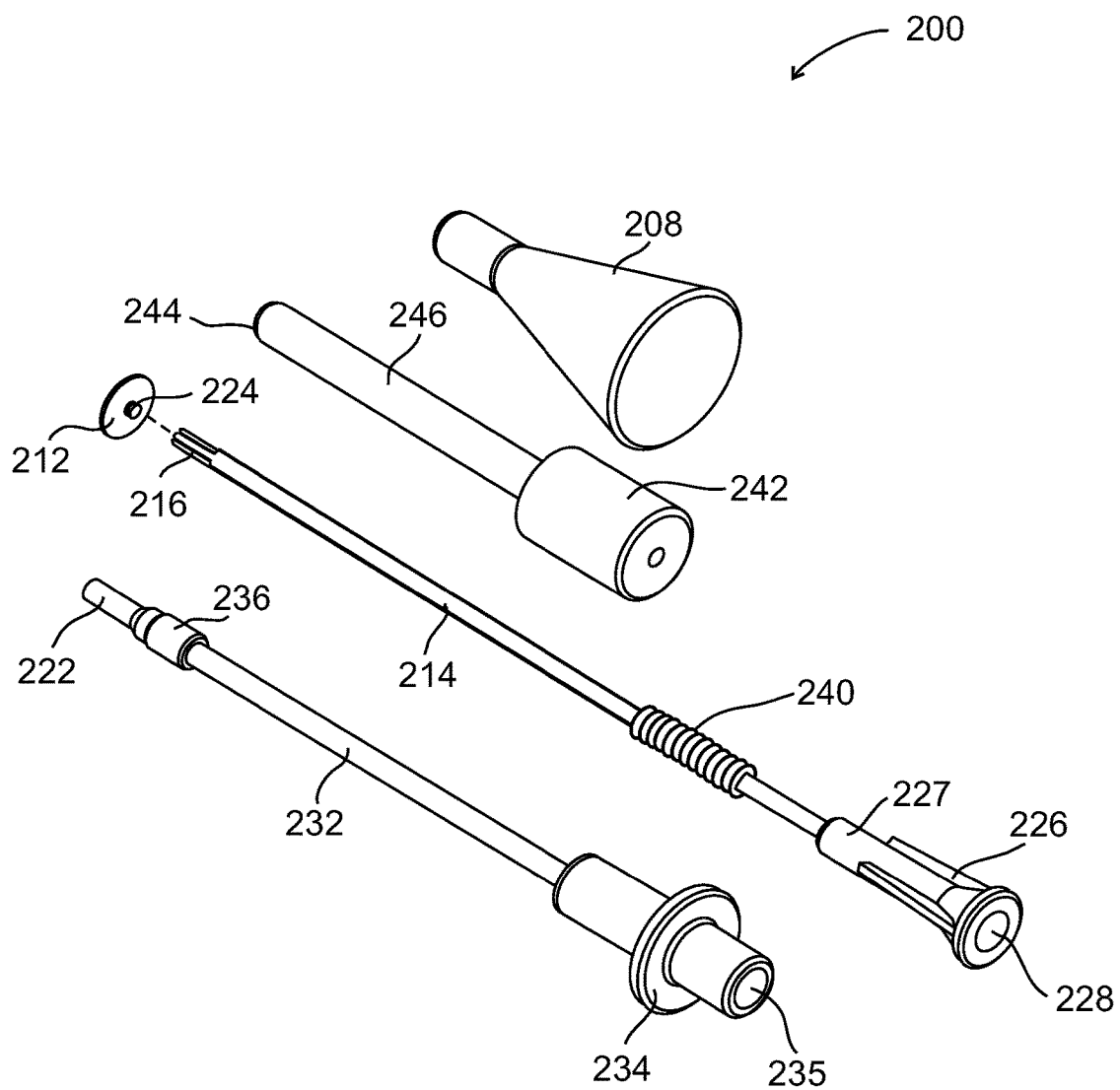
FIGS. 4A-4C schematically illustrate perspective views of the various mechanisms in the device of FIG. 3, according to some embodiments of the present invention.
Figure 4B:
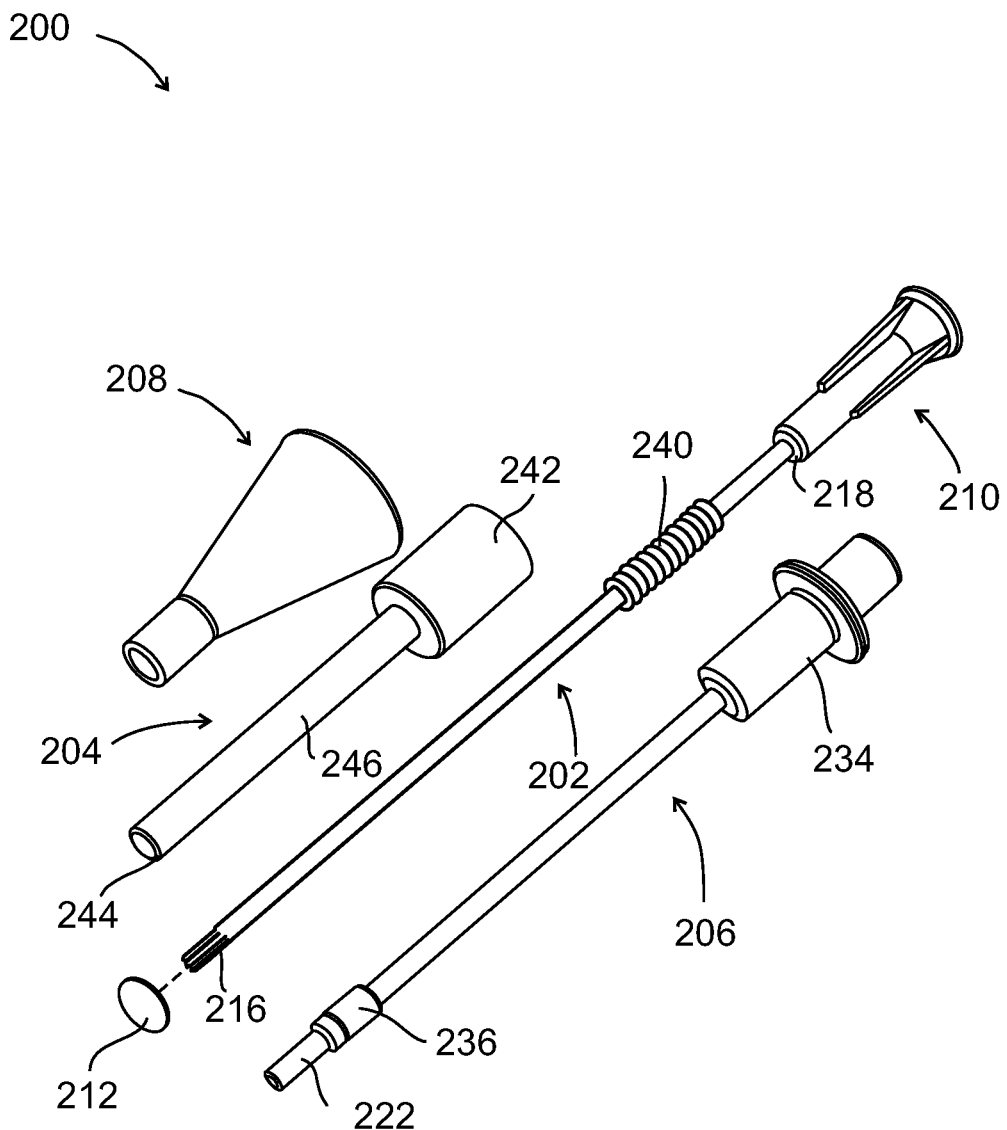
Figure 4C:
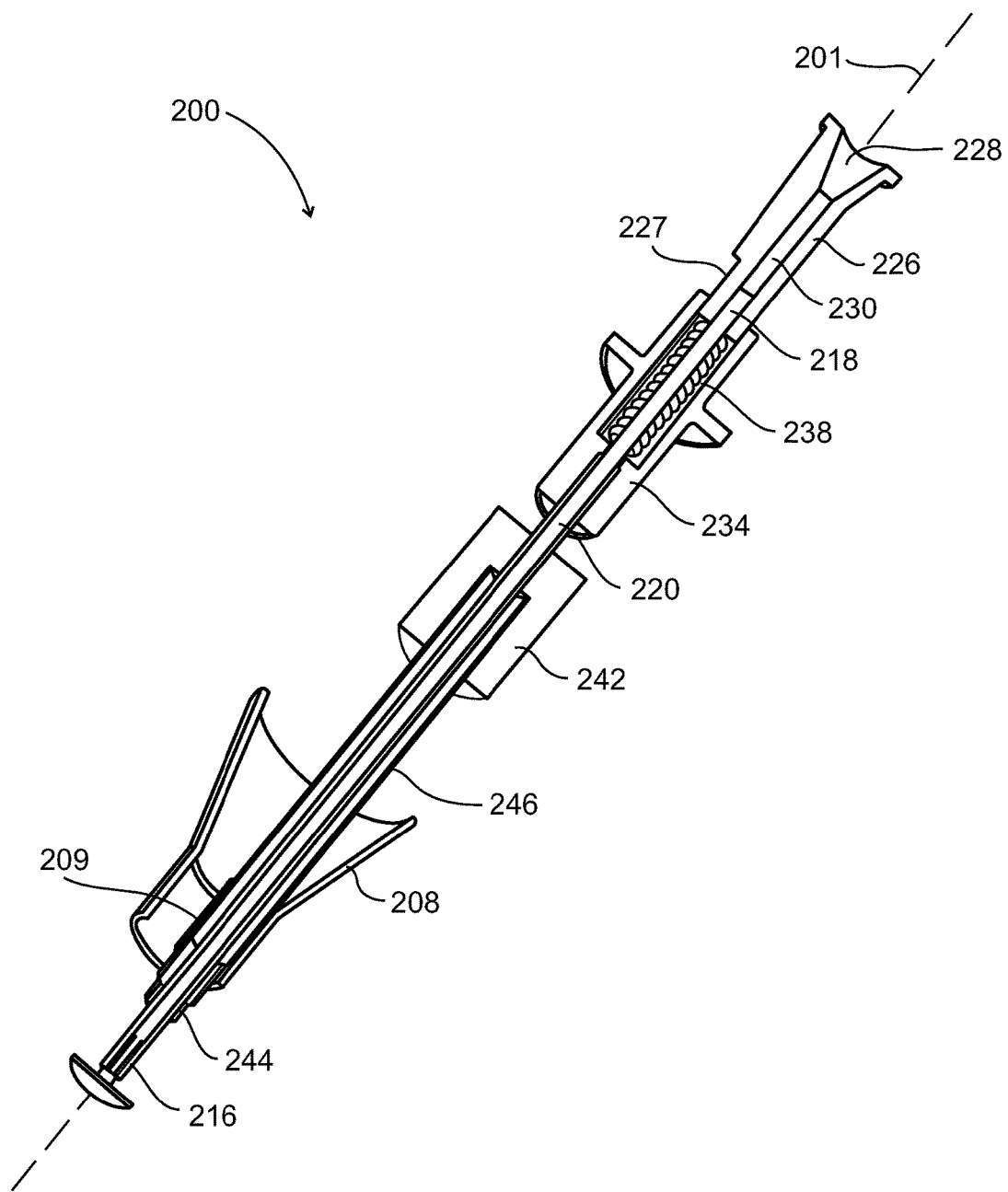

Reference is now also made to FIGS. 4A and 4B which schematically illustrate perspective views of the various mechanisms in the device; and to FIG. 4C which schematically illustrates a perspective, sectional view of tympanic membrane repair device 200; according to some exemplary embodiments of the present invention.

In some exemplary embodiments, patch guiding mechanism 202 includes a hollow rod 214 concentrically extending along longitudinal axis 201, and having a distal end 216, a proximal end 218, and a throughbore 220 interconnecting the proximal end and the distal end. Alternatively, rod 214 may be a solid rod when patch 212 is a self-adhering patch.

Optionally, rod 214 is of a diameter ranging from 1 mm-10 mm, for example, 2 mm, 3 mm, 4 mm, 5 mm, 7 mm, 8 mm, 9 mm. Optionally, distal end 212 is configured for attaching patch 212 to the distal end. For example, distal end 216 may include a spring-loaded clamping mechanism which forcedly clamps onto a projecting button 224 on patch 212 when a radial force is applied to the distal end, and which releases the projecting button when the radial force is removed.

In some exemplary embodiments, an adhesive insertion adaptor 226 included in adhesive application mechanism 210 is attached to proximal end 218. Optionally, adhesive insertion adaptor 226 includes an opening 228 and a conduit 230 extending through the adaptor. Optionally, the adhesive for adhering patch 212 is introduced into device 200 through opening 228, and flows through conduit 230 into throughbore 220 and out the distal end onto patch 212.

Figure 5:
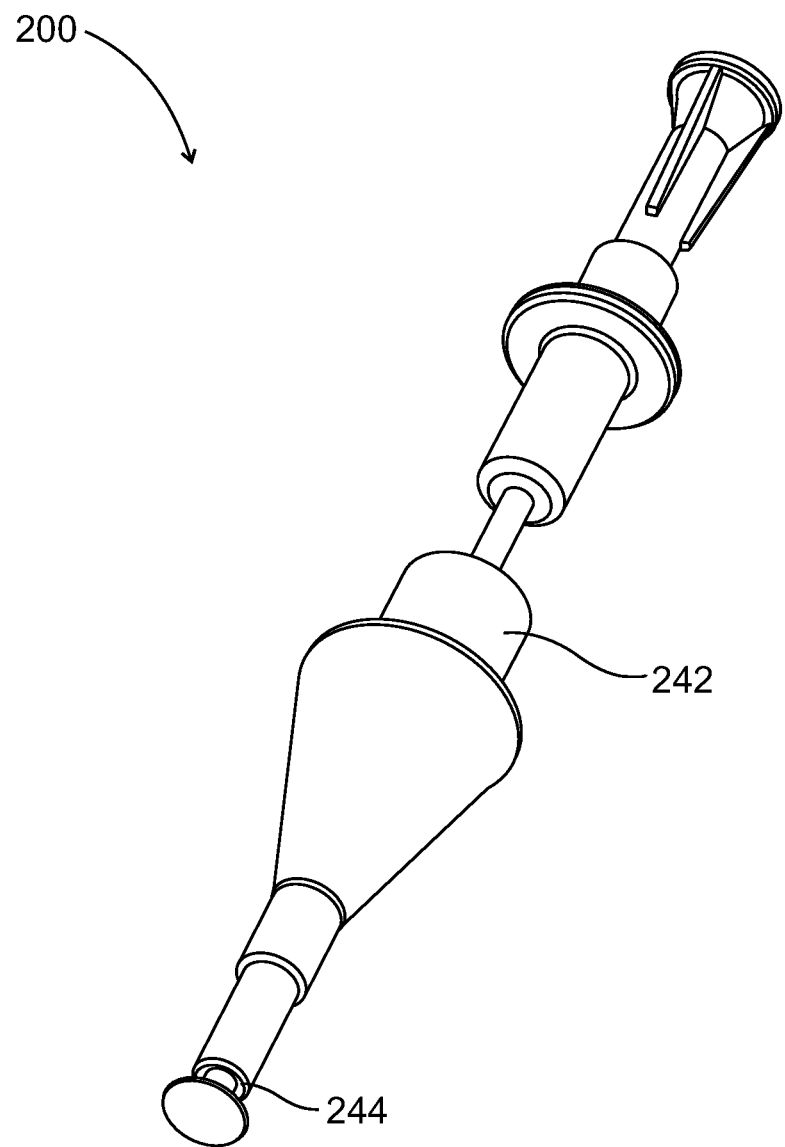
FIG. 5 schematically illustrates a perspective view of the tympanic membrane repair device of FIG. 3 in a debridement configuration, according to some exemplary embodiments of the present invention.

In some exemplary embodiments, debridement mechanism 204 includes a proximal rotary knob 242, a distal cutting blade 244, and a cylindrical tube 246 interconnecting the knob and the blade. Optionally, cylindrical tube 246 slidably fits over tube 232 in patch release mechanism 206 for moving debridement mechanism in the proximal and distal direction. Reference is now also made to FIG. 5 which schematically illustrates a perspective view of tympanic membrane repair device 200 in a debridement configuration, according to some exemplary embodiments of the present invention. Optionally, slidingly pushing rotary knob 242 towards patch 212 nears blade 244 to the tympanic membrane. Optionally, rotating rotary knob 242 rotates blade 244 cutting the peripheral tissue surrounding the perforation. Optionally, the cut tissue remains inside a periphery of blade 244. Optionally, pulling rotary knob 242 in a proximal direction retrieves blade 244 following debridement. Optionally, the cut tissue is retrieved with blade 244.

In some exemplary embodiments, patch release mechanism 206 includes a hollow tube 232 which slidably fits over rod 214. Optionally, hollow tube 232 is of a diameter ranging from 1.5 mm-11 mm, for example, 2.5 mm, 3.5 mm, 4.5 mm, 6.5 mm, 7.5 mm, 9.5 mm. Optionally, hollow tube 232 includes a proximal release lever 234, and a blade protector 236 distally positioned near a distal end 222. Optionally, release lever 234 includes a cylindrical shape and has a spring cavity 238 for accommodating a coil spring 240 proximally located on rod 214. Optionally, a cavity opening 235 is adapted to receive a distal portion 227 of adhesive insertion adaptor 226 for slidingly fitting into spring cavity 238 when release lever 234 is pulled in a proximal direction. Optionally, coil spring 240 is a compression spring and compresses inside spring cavity 238 as release lever 234 is pulled in the proximal direction and distal portion 227 slides into spring cavity 238.

Figure 6:
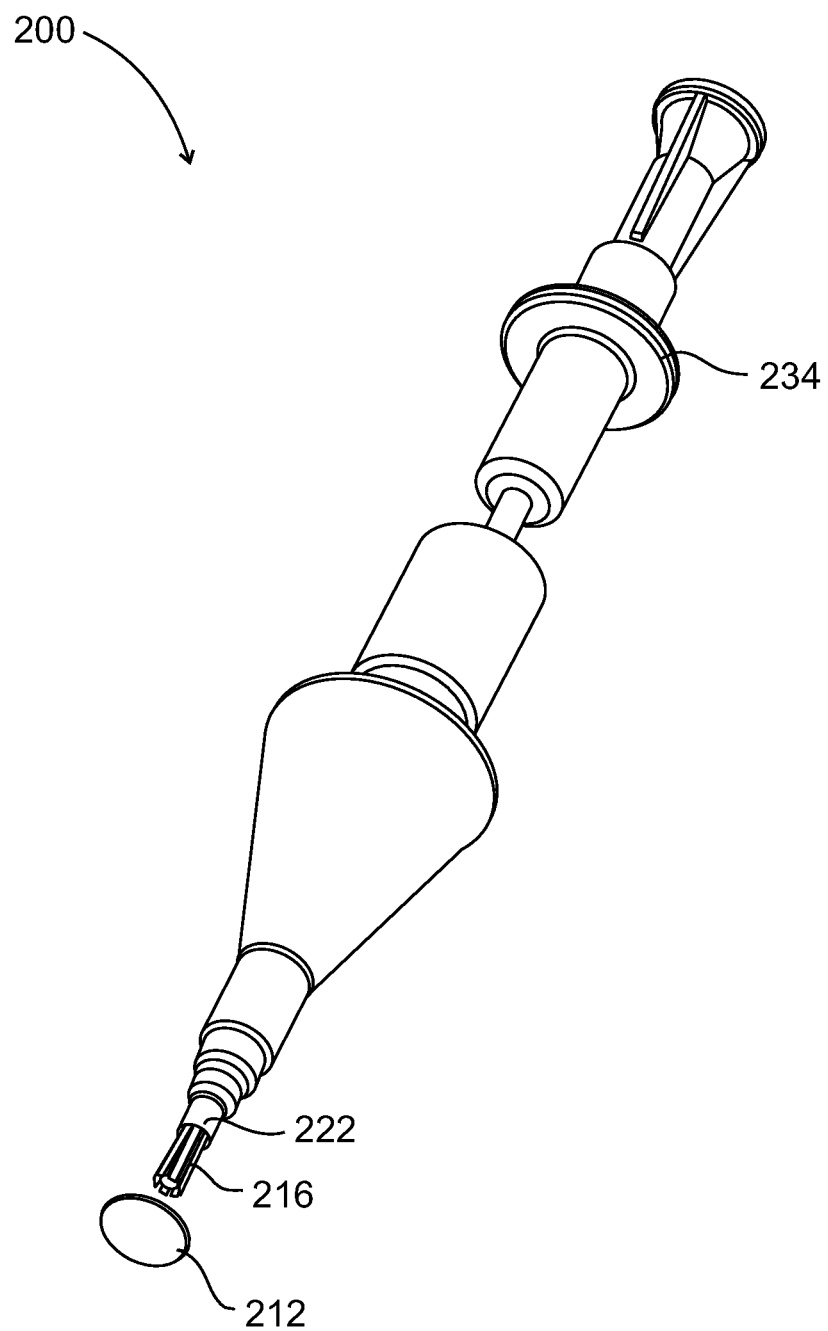
FIG. 6 schematically illustrates a perspective view of the tympanic membrane repair device of FIG. 3 in a patch release configuration, according to some exemplary embodiments of the present invention.

In some exemplary embodiments, when release lever 234 is not pulled in the proximal direction, coil spring 240 exerts a pushing force on hollow tube 232 in a direction towards distal end 216. Optionally, distal end 222 overlays distal 216 applying a radial force on distal end 216. Optionally, distal end 216 closes clasping button 224 on patch 212. Reference is now also made to FIG. 6 which schematically illustrates a perspective view of tympanic membrane repair device 200 in a patch release configuration, according to some exemplary embodiments of the present invention. Optionally, pulling release lever 234 in the proximal direction retrieves hollow tube 232 in the proximal direction, and distal end 222 from over distal end 216. Optionally, the radial force applied on distal end 216 for clasping button 224 is removed, releasing patch 212.

In some exemplary embodiments, device alignment mechanism 208 serves to maintain device 200 aligned and anchored in the auditory canal. Optionally, device alignment mechanism 208 is funnel shaped and includes an alignment receptacle 209 for slidingly accommodating cylindrical tube 246 and thereby maintaining device 200 aligned with the perforation. Optionally, a minimum diameter of alignment mechanism 208 ranges from 2 mm-15 mm, for example, 3 mm, 5 mm, 7 mm, 9 mm, 11 mm, 13 mm. Optionally, device alignment mechanism 208 includes a speculum or similar type of device known in the art. Optionally, device alignment mechanism 208 is fitted into the opening to the auditory canal. Optionally, a distance between a distal end of alignment mechanism 208 and patch 212 ranges from 10 mm-35 mm, for example, 15 mm, 20 mm, 25 mm, 30 mm.

Figure 7A:
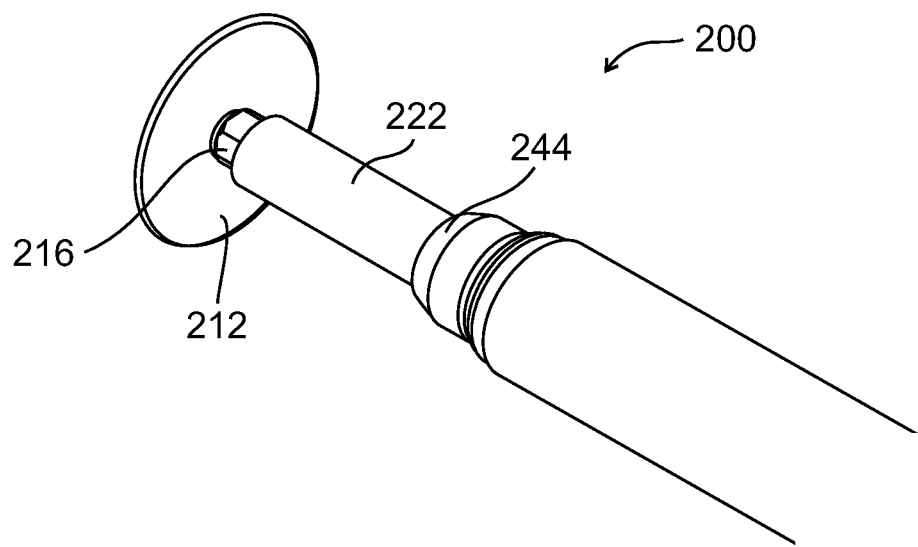
FIGS. 7A-7C schematically illustrate partial perspective views of the device in FIG. 3 in a patch guiding configuration, in a debridement configuration, and in a patch release configuration, respectively, according to some exemplary embodiments of the invention.
Figure 7B:
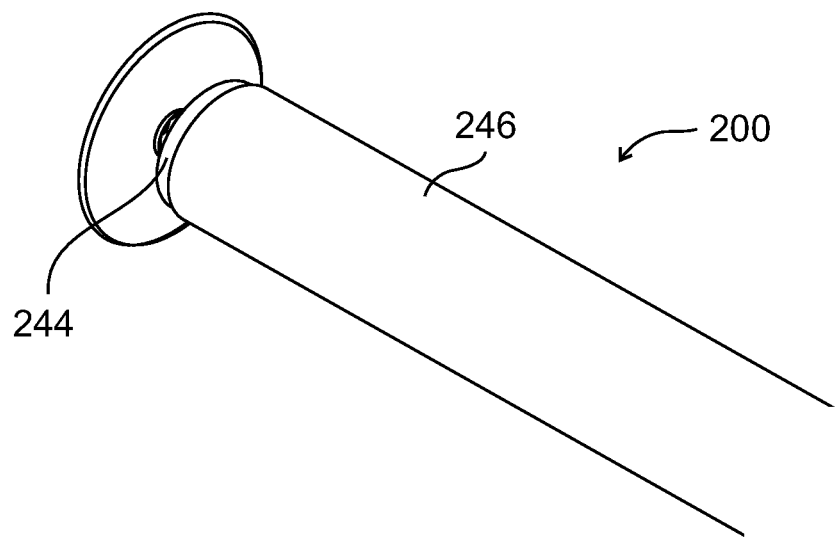
Figure 7C:
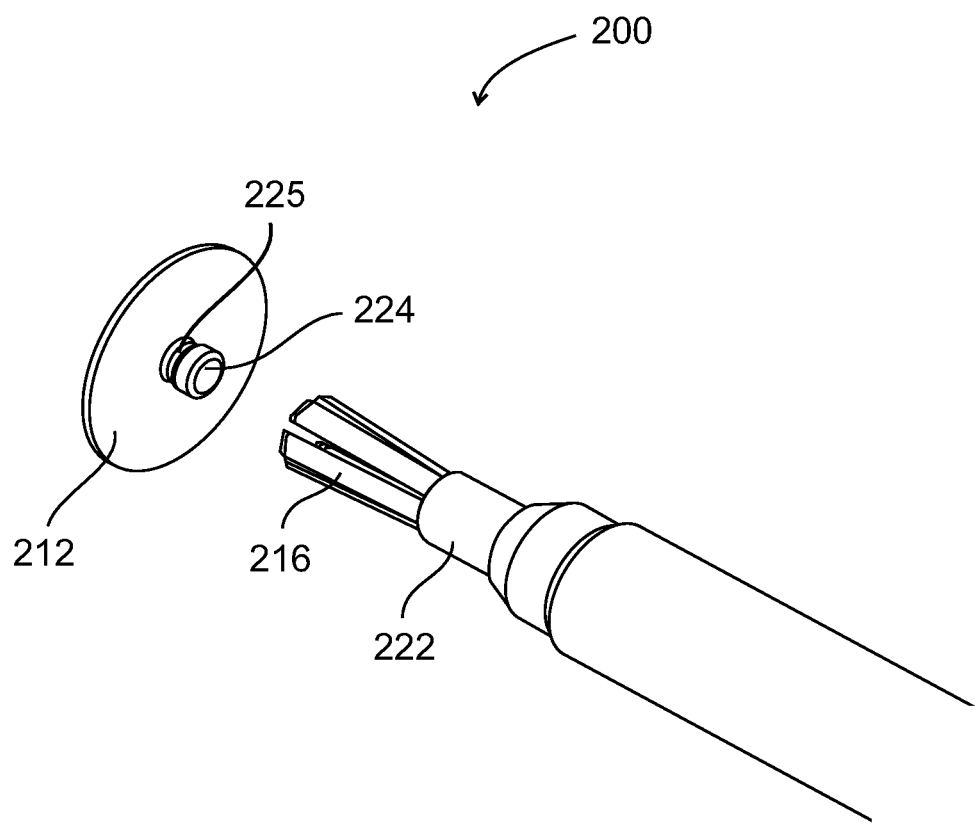

Reference is now made to FIGS. 7A-7C which schematically illustrate partial perspective views of device 200 in a patch guiding configuration, in a debridement configuration, and in a patch release configuration, respectively, according to some exemplary embodiments of the invention.

In some exemplary embodiments, as shown in FIG. 7A, patch 212 is secured in position by the clamping action of distal end 216 due to the spring-loaded clamping mechanism, with distal end 222 applying the radial force (pressing) on distal end 216. Blade 244 is retrieved. Optionally, in this configuration, device 200 is guided down the auditory canal and patch 212 inserted through the perforation in the tympanic membrane.

In some exemplary embodiments, as shown in FIG. 7B, cylindrical tube 246 is moved in the distal direction for nearing blade 244 to the debridement area in the tympanic membrane.

In some exemplary embodiments, as shown in FIG. 7C, distal end 222 has been slidingly moved in the proximal direction, uncovering distal end 216. The radial force applied by distal end 222 on distal end 216 is removed. Distal end 216 opens due to the spring-loaded clamping mechanism releasing button 224 on patch 212. Optionally, patch 212 has been adhered to the tympanic membrane. An annular recess 225 is formed between patch 212 and button 224 where a button 224 diameter is greater than a diameter of the annular recess.

Figure 8:
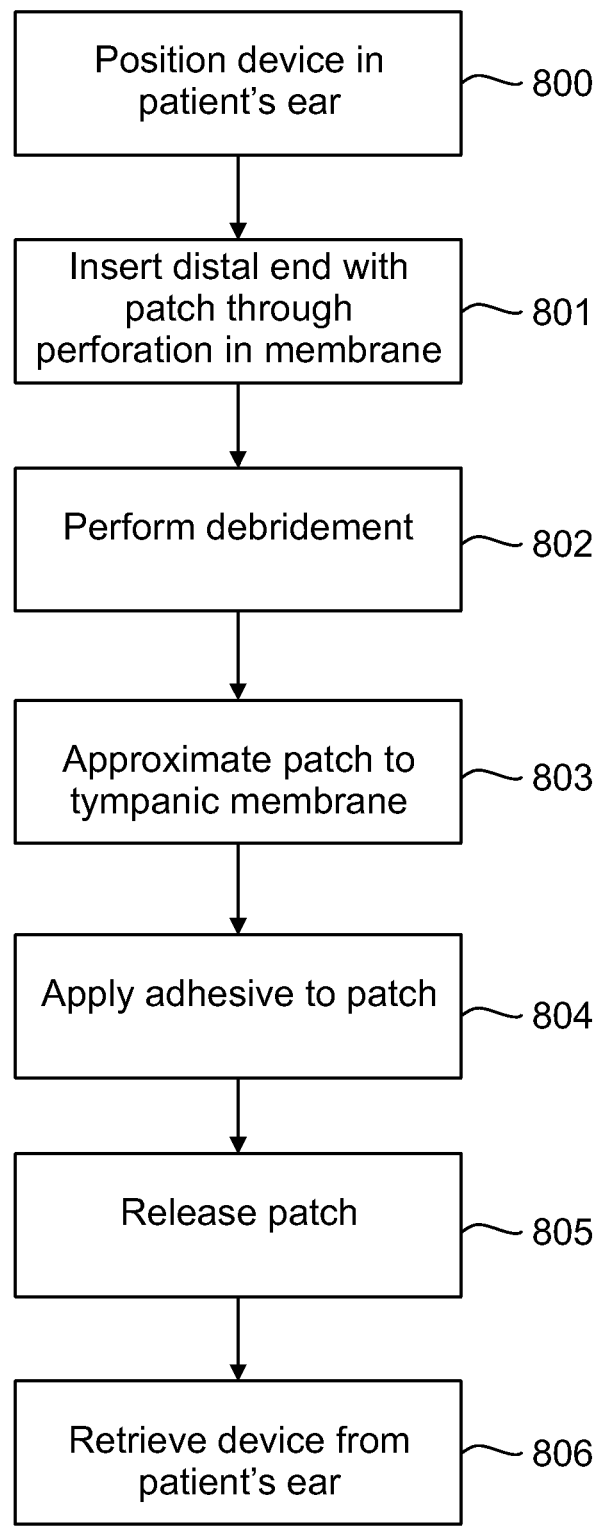
FIG. 8 illustrates a flow chart of a non-limiting method of repairing a perforation in a tympanic membrane by adhering a flexible patch to an undersurface of the membrane, according to some exemplary embodiments of the present invention.

Reference is now made to FIG. 8 which illustrates a flow chart of a non-limiting method of repairing a perforation in a tympanic membrane by adhering a flexible patch to an undersurface of the membrane, according to some exemplary embodiments of the present invention. Reference is also made to FIGS. 9A-11 which schematically illustrate the operation of tympanic membrane repair device 200 while performing the method, according to some exemplary embodiments of the present invention.

At 800, a physician optionally performs an otoscopy to locate the perforation and determines its size, and selects a patch 212 of a suitable dimension and attaches it to distal end 216. Alternatively, the physician performs the otoscopy for making a perforation. Optionally, the patch is selected so that it is at least 1 mm larger than the largest radius of the perforation. Optionally, attachment is done by pulling on release lever 234 so that distal end 222 moves in a proximal direction away from distal end 216. Distal end 216 opens and button 224 in patch 212 is inserted into the distal end. Optionally, release lever 234 is returned to its original "closed" position, distal end 222 moving distally over 216 pressing distal end 216 closed over button 222, securing patch 212. Optionally, patch 212 is pre-attached to distal end 216. The physician then inserts device 200 into the patient's ear first introducing the end of the device to which patch 212 is attached.

At 801, the physician guides patch 212 down the auditory canal and through the perforation in the tympanic membrane. Optionally, the physician utilizes a micro-otoscope to monitor the medical procedure. Optionally, the micro-otoscope is mechanically attached to device 200. Alternatively, the micro-otoscope is separately inserted into the auditory canal. Optionally, a position of device 200 is adjusted by the physician and is maintained aligned/anchored by device alignment mechanism 208 which is fitted into the opening of the auditory canal.

Figure 9A:
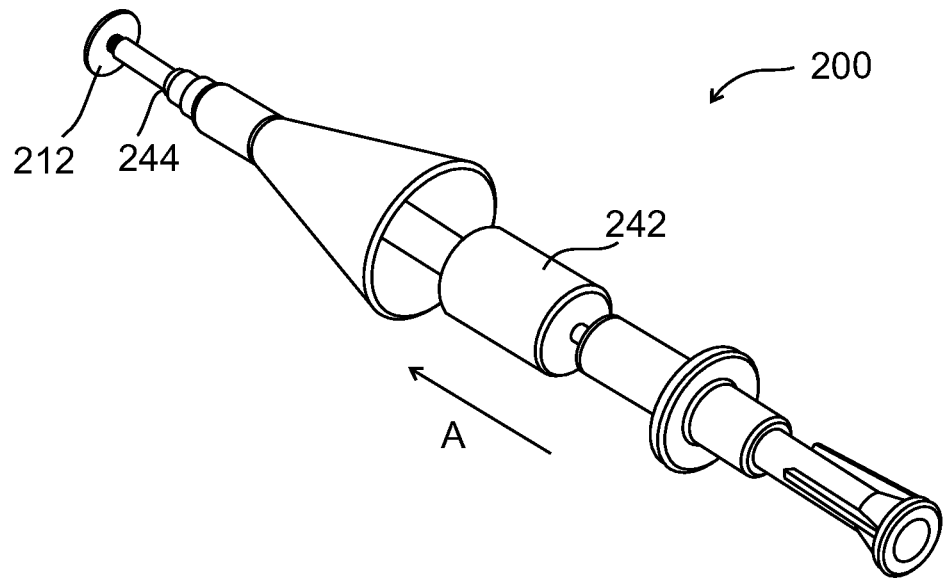
FIGS. 9A and 9B, 10A and 10B, 11A and 11B, and 12 schematically illustrate the operation of the tympanic membrane repair device in FIG. 3, according to some exemplary embodiments of the present invention.
Figure 9B:
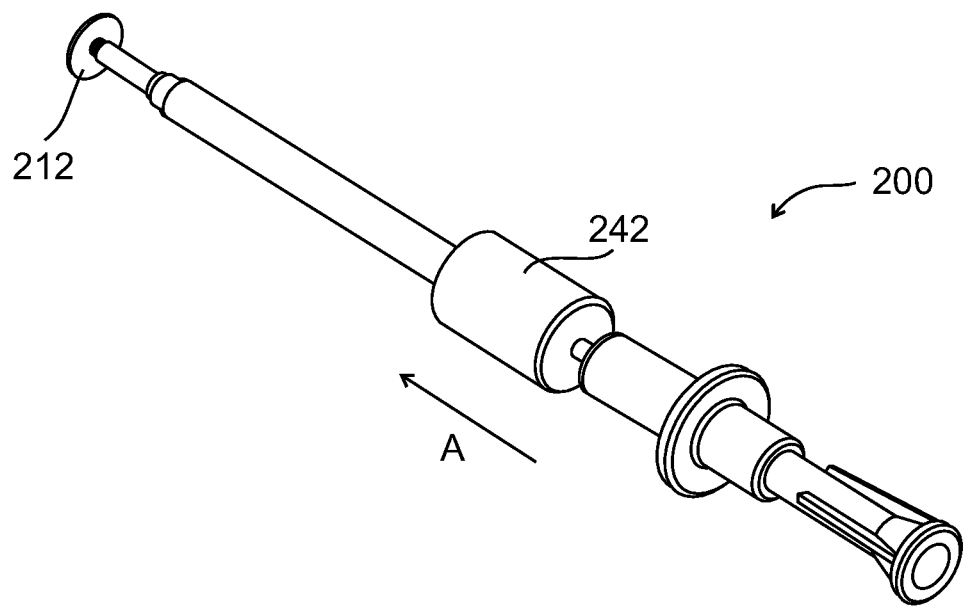
Figure 10A:
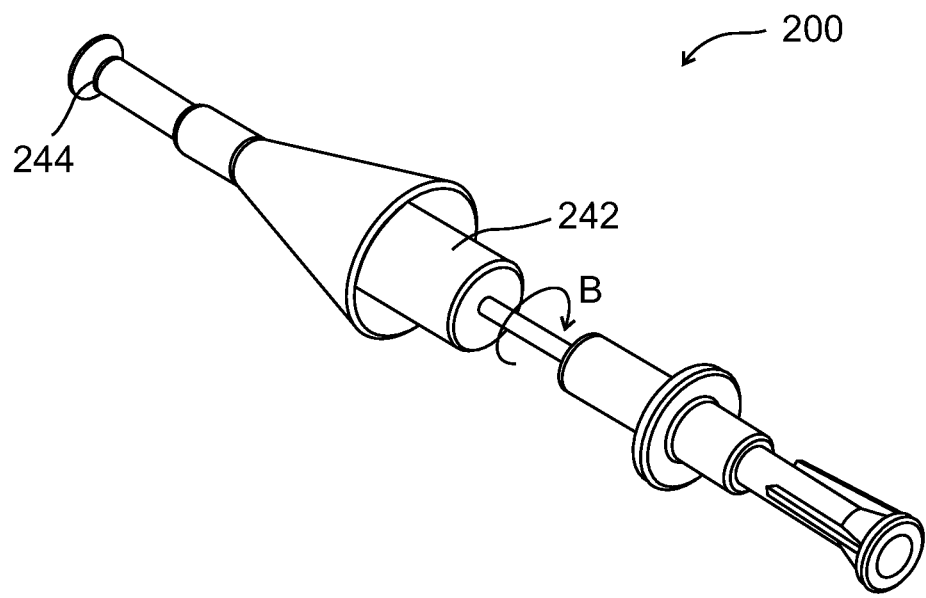
Figure 10B:
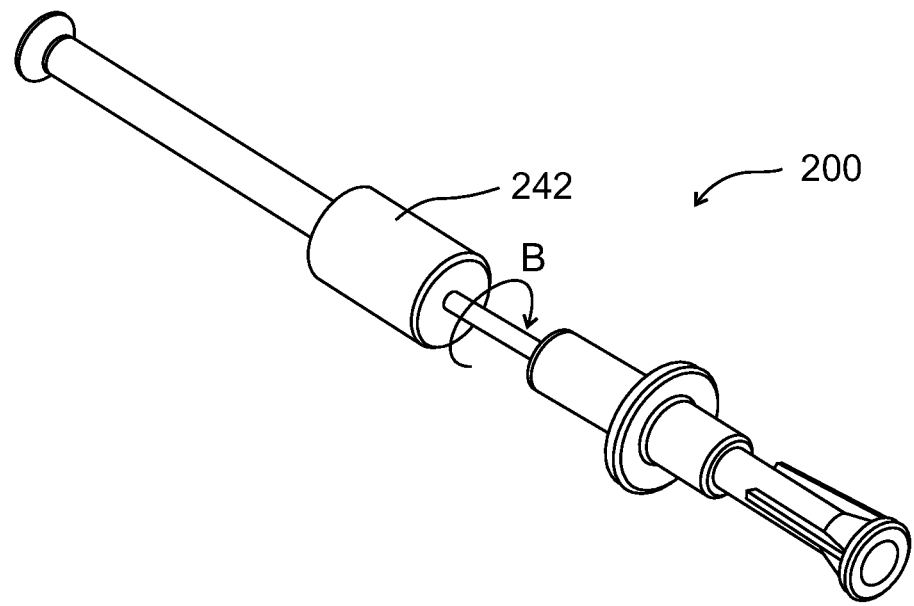

At 802, the physician performs debridement of the tissue surrounding the perforation. In some exemplary embodiments, as shown in FIGS. 9A and 9B, once device 200 has been inserted down the auditory canal and patch 212 inserted through the perforation in the tympanic membrane, debridement of the tissue surrounding the perforation is done. A first step in debridement includes moving rotary knob in a distal direction A for nearing blade 244 to the membrane. In some exemplary embodiments, as shown in FIGS. 10A and 10B, once blade 244 has been neared to the tympanic membrane, rotary knob 242 is rotated in a clockwise direction B for cutting away the peripheral tissue. In some exemplary embodiments, cutting of the tissue may be done by rotating rotary knob 242 in a counterclockwise direction. Optionally, cutting is done by a reciprocating motion both in a clockwise direction and a counterclockwise direction. In some exemplary embodiments, cutting of the tissue may not require rotating rotary knob 242. Optionally, pushing rotary knob 242 in the distal direction also results in cutting of the tissue. Optionally, the cut tissue is fitted within the periphery of the cutting edge of blade 244. Alternatively, the physician inserts a cutting instrument for debriding, for example, a blade, scissors, or other instrument known in the art suitable for performing debridement of the perforation.

At 803, the physician aligns device 200 so that patch 212 is proximal to the area of the perforation, on the undersurface of the tympanic membrane.

Figures 11A, 11B:
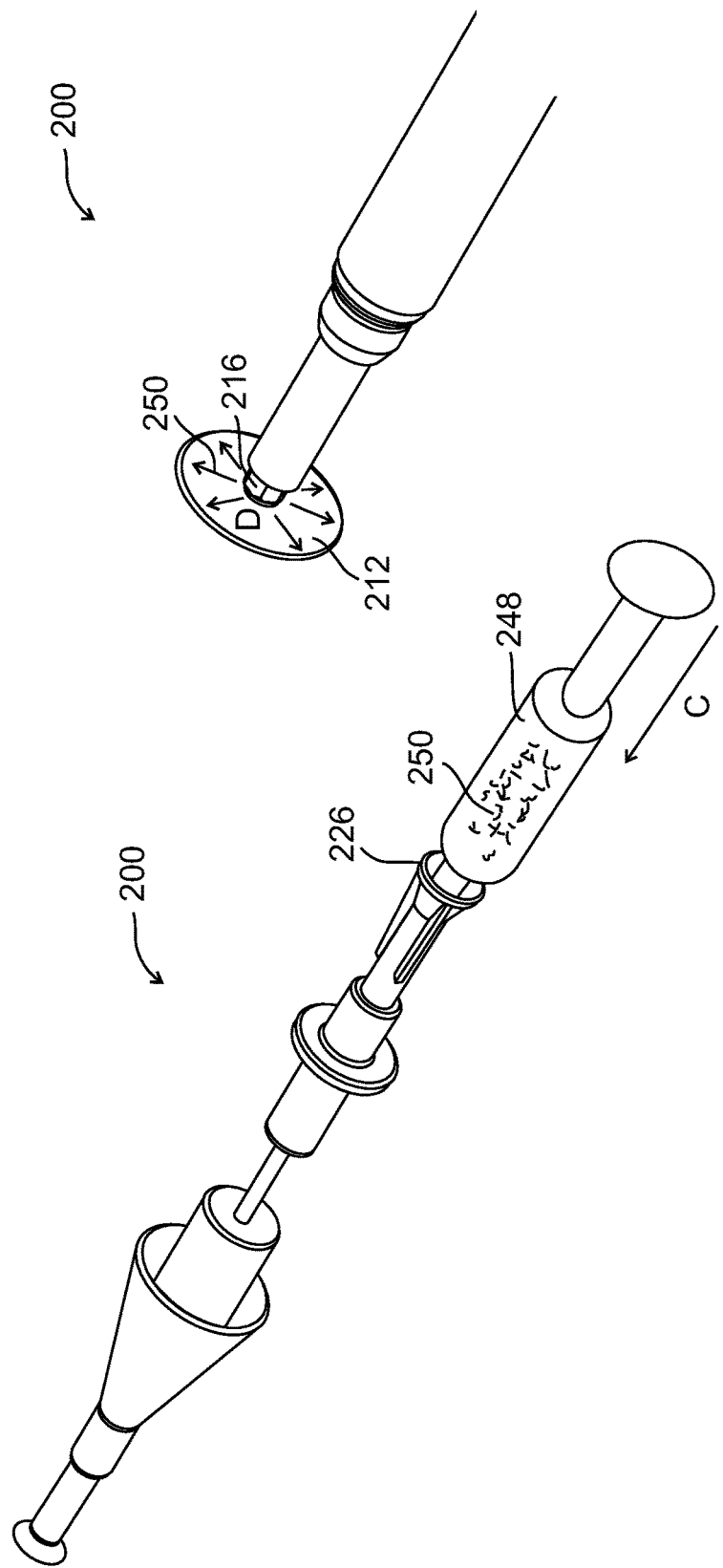

At 804, the physician applies adhesive to patch 212. In some exemplary embodiments, as shown in FIGS. 11A and 11B, following debridement and for adhering patch 212 to the undersurface of the tympanic membrane, the physician attaches an adhesive container 248 with an adhesive 250 to adhesive insertion adapter 226. Optionally, adhesive container 248 includes a capsular container. Optionally, adhesive container 248 includes a syringe and a plunger which is pushed in the distal direction, as shown by arrow C, for administering adhesive 250. Optionally, the capsular container is fittedly accommodated in the syringe. Optionally, the adhesive is an "instant" glue. Optionally, adhesive 250 is introduced into device 200 and flows through the device and out distal end 216, spreading over the surface of patch 212, as shown by arrows D. Optionally, steps 1203 and 1204 are interchangeable. Alternatively, patch 212 is self-adhering and there is no need for the adhesive insertion adapter 226 or for the administering of the adhesive into device 200.

Figure 12:
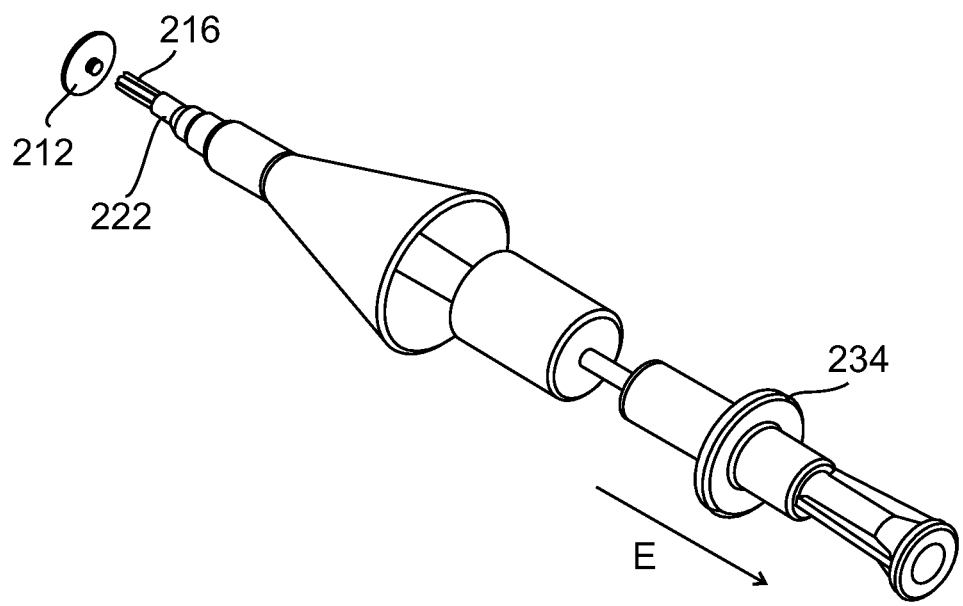

At 805, patch 212 is attached to the undersurface of the tympanic membrane sealing the perforation. Optionally, device 200 is pulled in a proximal direction for attaching patch 212 to the undersurface. Optionally, patch 212 adheres "instantly" to the undersurface by the instant glue. In some exemplary embodiments, as shown in FIG. 12, following adhering of patch 212 and for releasing the patch, patch release lever 234 is pulled in a proximal direction E.

Optionally, distal end 222 is pulled in the proximal direction E uncovering distal end 216, which opens as the radial force is removed from the spring-loaded clamping mechanism. Optionally, opening of distal end 216 releases button 224 on patch 212, releasing the patch. Alternatively, device 200 is pulled in the proximal direction after waiting a predetermined amount of time for adhering of patch 212 to the undersurface, the patch detaching due to the resistance of the undersurface to the pulling.

At 806, the physician retrieves device 200 from the auditory canal. In some exemplary embodiments, device 200 is retrieved only after waiting a predetermined amount of time following attachment of patch 212 to the undersurface for complete adhesion. Alternatively, biodegradable foam is introduced into the middle ear for supporting patch 212 as it adheres to the tympanic membrane.

Figure 13:
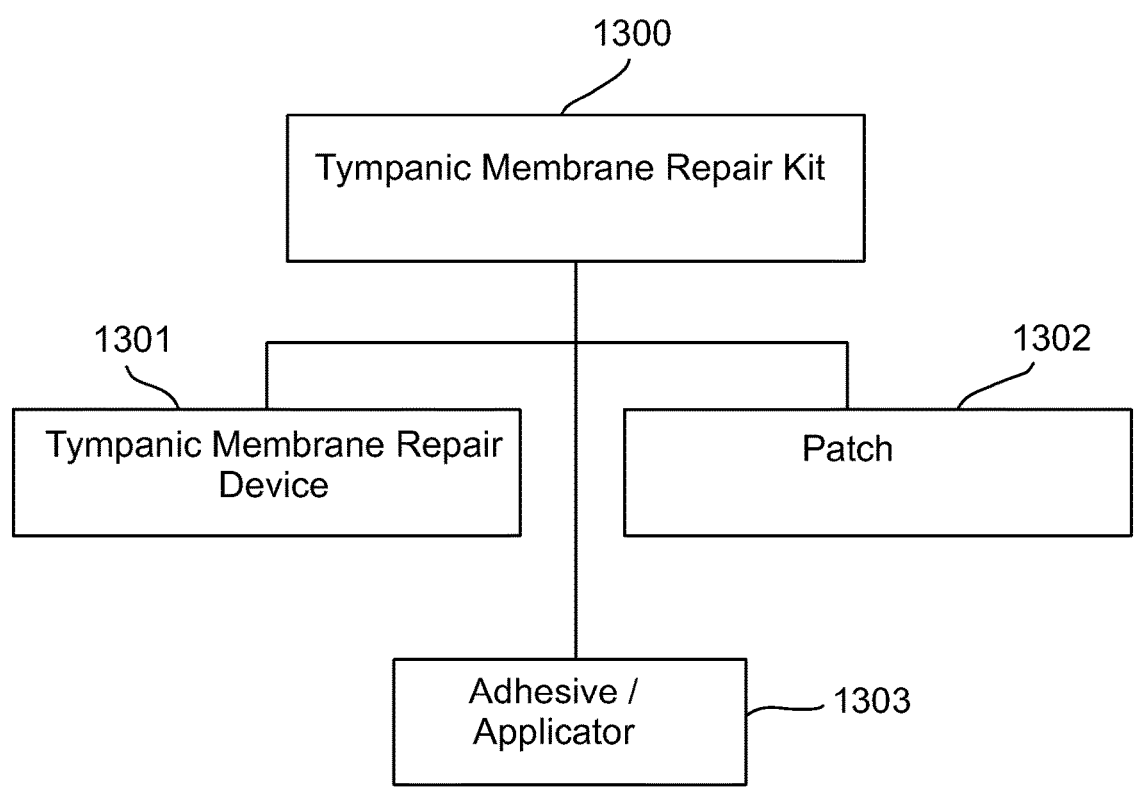
FIG. 13 schematically illustrates a tympanic membrane repair kit, according to some exemplary embodiments of the invention.

Reference is now made to FIG. 13 which schematically illustrates a tympanic membrane repair kit 1300, according to some exemplary embodiments of the invention. In some exemplary embodiments, kit 1300 is a single use kit which is disposed of following one-time usage. Kit 1300 includes a tympanic membrane repair device 1301, which may be similar to that shown in FIG. 1 at 100, or in FIG. 3 at 200. Optionally, kit 1300 includes one or more patch 1302, for example, 2, 3, 4, 5 patches. Optionally, patch 1302 includes patches of different sizes, for example, having a diameter in a range from 2 mm-10 mm, for example 3 mm, 4 mm, 5 mm, 6 mm, 8 mm, 9 mm. Alternatively, the patch is a single-sized patch. Optionally, kit 1300 includes an adhesive and an adhesive applicator 1303.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A kit comprising:
a patch that comprises a clasp for pulling the patch against an undersurface of the tympanic membrane, wherein said clasp comprises a clasp proximal portion and a clasp distal portion; and
a device comprising:
a patch guiding mechanism including:
(a) a rod for inserting said patch through a perforation in the tympanic membrane,
(b) at least one securing arm that comprises an arm distal portion and an arm proximal portion, and
(c) a first tube surrounding said rod and said at least one securing arm,
a rotatable debridement mechanism including:
(d) a second tube that surrounds said first tube,
(e) at least one cutting edge attached to a distal end of the second tube for cutting tissue surrounding the perforation when said rotatable debridement mechanism is rotated, and
(f) a knob attached to the proximal end of the second tube, to enable a user to rotate the rotatable debridement mechanism; and wherein:
the pulling of the patch is facilitated by said first tube securing said clasp to said rod by preventing said clasp proximal portion from moving past said arm distal portion, and said patch is released from said rod when said first tube is moved proximally along a longitudinal axis of said rod, thereby releasing said clasp proximal portion from said patch guiding mechanism.

2. A kit according to claim 1, wherein said at least one securing arm is disposed at a distal end of said rod, and is adapted to accommodate mechanical coupling of said patch, and wherein said at least one securing arm serves as a spring-loaded clamp for grasping said patch.

3. A kit according to claim 1, further comprising a patch release mechanism that includes a release lever for proximally pulling said first tube.

4. A kit according to claim 1, including an alignment mechanism for substantially axially aligning the device when inserted in the auditory canal.

5. A kit according to claim 4, wherein said device alignment mechanism includes an alignment receptacle for aligning said patch guiding mechanism with the perforation.

6. A kit according to claim 4, wherein said device alignment mechanism includes a speculum.

7. A kit according to claim 1, including an adhesive application mechanism for administering an adhesive through the device to the patch.

8. A kit according to claim 7, wherein said adhesive application mechanism includes an adhesive insertion adapter through which said adhesive is configured to be poured into the device.

9. A kit according to claim 8, wherein said adhesive insertion adapter is attached to a hollow rod in said patch guiding mechanism having a conduit fluidly connecting said adhesive insertion adapter with the patch.

10. A kit according to claim 1, wherein the patch includes hyaluronic acid.

11. A kit according to claim 1, wherein the device is configured for disposing following a single use.

12. A kit comprising:
a patch that comprises a clasp for pulling the patch against an undersurface of the tympanic membrane, wherein said clasp comprises a clasp proximal portion and a clasp distal portion, wherein said clasp proximal portion is button-shaped, wherein said clasp distal portion forms an annular recess between said patch and said clasp proximal portion, and wherein a button diameter of said clasp proximal portion is greater than a diameter of the annular recess; and
a device comprising:
a patch guiding mechanism including:
(a) a rod for inserting said patch through a perforation in the tympanic membrane,
(b) at least one securing arm that comprises an arm distal portion and an arm proximal portion, wherein said arm distal portion is configured to secure said clasp distal portion, and
(c) a first tube surrounding said rod and said at least one securing arm,
a rotatable debridement mechanism including:
(d) a second tube that surrounds said first tube,
(e) at least one cutting edge attached to a distal end of the second tube for cutting tissue surrounding the perforation when said rotatable debridement mechanism is rotated, and
(f) a knob attached to the proximal end of the second tube, to enable a user to rotate the rotatable debridement mechanism; and wherein:
the first tube is configured to slidably cover said rod and said at least one securing arm thereby applying a radial force for securing said clasp,
the pulling of the patch is facilitated by said first tube securing said clasp to said rod by preventing said clasp proximal portion from moving past said arm distal portion, and
said patch is released from said rod when said first tube is moved proximally along a longitudinal axis of said rod, thereby releasing said clasp proximal portion from said patch guiding mechanism.

* * * * *